United States Patent [19]

Sheehan et al.

[11] 4,164,445

[45] Aug. 14, 1979

[54] ETHANOL AS THE MAJOR SOURCE OF CARBON AND ENERGY IN PENICILLIN PRODUCTION

[75] Inventors: Brian T. Sheehan; Judith Baymiller; Robert W. Eltz, all of Princteon, N.J.

[73] Assignee: E. R. Squibb & Sons, Inc., Princeton, N.J.

[21] Appl. No.: 562,540

[22] Filed: Mar. 27, 1975

[51] Int. Cl.$^2$ .............................................. C12D 9/10
[52] U.S. Cl. ....................................... 435/46; 435/935
[58] Field of Search ............... 195/81, 36 R, 49, 36 P, 195/115

[56] References Cited

U.S. PATENT DOCUMENTS

| 2,674,561 | 4/1954 | Moyer | 195/36 R |
|---|---|---|---|
| 3,024,169 | 3/1962 | Demain et al. | 195/36 P |
| 3,563,857 | 2/1971 | Oki et al. | 195/49 |
| 3,595,751 | 7/1971 | Nakayama et al. | 195/49 |
| 3,682,777 | 8/1972 | Nara et al. | 195/36 P |
| 3,843,441 | 10/1974 | Kubota et al. | 195/30 |
| 3,844,893 | 10/1974 | Hitzman | 195/81 X |

FOREIGN PATENT DOCUMENTS 2048897  3/1971  France ..................................... 195/49

OTHER PUBLICATIONS

Demain, "Biosynthesis of Penicillins and Cephalosporins", *Biosynthesis of Antibiotics*, Academic Press, New York, London, Snell ed. vol. 1, (1966), pp. 30–42.

Majumdar et al., "Utilization of Carbon and Nitrogen-containing Compounds for Neomycin Production by *Streptomyces Fradiae*"; *App. Microbiology*, vol. 15, No. 4, (1967), pp. 744–749.

Katz et al., "The Role of Nutrition in the Synthesis of Actinomycin", *App. Microbiology*, vol. 6 (1958), pp. 236–241.

Perlman, "Chemically Defined Media for Antibiotic Production", *Ann. N.Y. Acad. Sci.*, vol. 139 (1), (1966), pp. 258–269.

*Primary Examiner*—Thomas G. Wiseman
*Attorney, Agent, or Firm*—Lawrence S. Levinson; Stephen B. Davis

[57] ABSTRACT

Ethanol is employed as the major source of carbon and energy in the fermentative biosynthesis of penicillins.

5 Claims, No Drawings

ETHANOL AS THE MAJOR SOURCE OF CARBON AND ENERGY IN PENICILLIN PRODUCTION

BACKGROUND OF THE INVENTION

Penicillins are conventionally prepared by microbial synthesis in a nutrient medium containing a source of carbon and energy, a source of nitrogen as well as other ingredients such as inorganic salts and precursors. Various media have been successfully employed for this purpose in which the source of carbon and energy is a mixture of cornsteep liquor and carbohydrates such as lactose, glucose, dextrin and starch (see Perlman, "Chemically Defined Media For Antibiotic Production," Ann. N.Y. Acad. Sci., Vol. 139 (1), p. 258–269 (1966)). Other materials reported as successful carbon sources include sucrose, molasses, sorbitol, maltose, fructose, starch hydrolysate, and organic acids such as acetic and lactic.

Ethanol has previously been employed as the major source of carbon and energy in the fermentative production of various amino acids, for example, U.S. Pat. No. 3,563,857 to Oki et al. directed to the production of L-glutamic acid, U.S. Pat. No. 3,595,751 to Nakayama et al. directed to the production of L-lysine, U.S. Pat. No. 3,843,441 to Kubota et al. directed to the production of L-serine, and French Pat. No. 2,048,897 to Ajinomoto Co. directed to the production of L-threonine. Ethanol has also been employed in conjunction with the conventional carbohydrate carbon and energy sources listed above in the fermentative production of organic acids such as citric in U.S. Pat. No. 2,674,561 to Moyer. However, ethanol has not been previously reported as utilizable in the production of penicillins. In fact, ethanol has been stated to be unsuitable as a carbon and energy source in the production of the antibiotics actinomycin (Katz et al., "The Role of Nutrition in the Synthesis of Actinomycin," Applied Microbiology, Vol. 6, p. 236–241 (1958) and neomycin (Majumdar et al., "Utilization of Carbon and Nitrogen-containing Compounds for Neomycin Production by *Streptomyces fradiae*," Applied Microbiology, Vol. 15, p. 744–749, (1967)).

SUMMARY OF THE INVENTION

This invention is directed to the use of ethanol as the major source of carbon and energy in the biosynthesis of penicillins.

The advantages arising from the use of ethanol rather than the conventional carbon and energy sources listed above are numerous. These conventional materials can contain various impurities such as color bodies, minerals, and other components which may adversely affect the fermentation process or subsequent process steps for recovery of product. Ethanol, on the other hand, is commercially available as a consistently pure material so that there are few variations in the fermentation process from batch to batch. Ethanol is a liquid of a low order of viscosity thus permitting easy handling from storage to the fermentor when compared to the more viscous carbohydrate solutions of the prior art. Also, it is easy to sterilize the ethanol and thus ensure a feedstream of high purity and limit the possibility of contaminating the fermentation broth.

DETAILED DESCRIPTION

This invention is directed to producing penicillins by conventional fermentative biosynthetic processes except that ethanol is employed as the major carbon and energy source during the fermentation. By major carbon and energy source, it is meant that although small amounts of utilizable carbon may be present in the precursor, initial germination ingredients, and batched ingredients, once the fermentation has begun the ethanol provides at least fifty percent of the carbon and chemical energy to the fermentation.

By conventional fermentative process it is meant that the process conditions and other ingredients such as the nitrogen-source, precursor, and inorganic salts are those commonly employed in the production of penicillins.

As the nitrogen source various kinds of inorganic or organic salts or compounds such as urea, liquid ammonia, or ammonium salts such as ammonium chloride, ammonium sulfate, ammonium nitrate, ammonium acetate, ammonium phosphate, etc., may be employed.

Inorganic salts which may be added to the culture medium include magnesium sulfate, sodium phosphate, potassium monohydrogen phosphate, potassium dihydrogen phosphate, iron sulfate, manganese chloride, calcium chloride, calcium carbonate, sodium chloride, zinc sulfate, etc.

Culturing is conducted under aerobic conditions, such as aerobic shaking of the culture or aeration of a submerged culture with agitation. The temperature employed can vary from about 20° C. to about 28° C. and the pH can be from about 5.0 to about 7.5. Culturing is generally carried out for from about 5 to about 10 days.

This process can employ various penicillin producing cultures and in particular those of the Penicillium type with *Penicillium chrysogenum* being preferred. Suitable precursors include phenyl acetic acid and phenoxy acetic acid and salts thereof such as alkali metal (e.g. sodium, potassium, etc.) or alkaline earth metal (e.g. calcium, etc.) salts. By varying the precursor different forms of penicillin are produced. Preferably the penicillin produced is of the following formula:

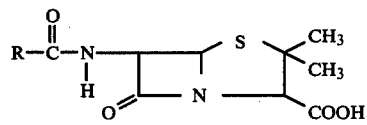

wherein R is $C_6H_5OCH_2-$, i.e. Penicillin V, or $C_6H_5CH_2-$, i.e. Penicillin G, or their pharmaceutically acceptable salts.

The following examples are illustrative of the invention. All temperatures are on the centigrade scale and percentages are on weight/volume basis unless otherwise noted.

EXAMPLE 1

Utilization of Ethanol In The Production Of Penicillin G

*Penicillium chrysogenum* ATCC 20444 (a sample of this culture is available from the American Type Culture Collection, Rockville, Md.) is employed as the seed microorganism. The seed culture medium contains 3.5% cornsteep liquor (as is), 1.8% glucose, 0.5% ammonium sulfate, 0.35% calcium carbonate, 0.004% soybean oil. Fifty (50) ml. of the sterile seed culture medium contained in a 250-ml. Erlenmeyer flask is inoculated with 0.5 ml. of a 0.1% peptone-water suspension of spores. Culturing is conducted on a rotary shaker with 2 inch diameter at 300 rpm for about 35 hours. Fifteen of these flask cultures are pooled to produce 700 ml. of inoculum for two 14-liter New Brunswick Scientific stirred-jar fermentors each containing 10 liters of a medium having the following composition:

| | |
|---|---|
| Cornsteep Liquor | 1.8% |
| $(NH_4)_2SO_4$ | 0.18% |
| Glucose hydrate | 0.20% |
| $CaCO_3$ | 0.03% |
| $Ca(OH)_2$ | 0.05% |
| Lard Oil | 0.4% |
| $NaH_2PO_4$ | 0.06% |
| $KH_2PO_4$ | 0.06% |
| UCON Lubricant 625 (Union Carbide) | 0.02% |

The pH of the medium is adjusted to 6.1 with sodium hydroxide before inoculation.

Culturing is carried out for 120 hours at 25° with aeration of 8 liters per minute and agitation of 700 rpm. The pH is controlled at not less than 5.8 and not more than 7.1 by the addition when necessary of either 10% sodium hydroxide or 10% sulfuric acid solutions. An aqueous feed stream containing 10% v/v ethanol (95%) sterilized by filtration is administered to one fermentor initiating at 12 hours of fermentation at a rate of 30 cc/hour and increasing to 120 cc/hour by 120 hours of fermentation. This feed is not administered to the control fermentation in the second fermentor. A salt solution containing 150 mg./ml. ammonium sulfate, 8 mg./ml. potassium dihydrogen phosphate and 8 mg./ml. sodium dihydrogen phosphate is administered to both fermentations as required to maintain broth supernatant ammonium-nitrogen and inorganic phosphate levels of at least 300 mg. $NH_3$-N/liter and 300 mg. P/liter. Precursor feed, 12.5% potassium phenyl acetate, is initiated at 12 hours of fermentation at a rate of 10 cc/8 hours to provide for production of penicillin G. Withdrawals are made as necessary to maintain the 10-liter working volume. By 119 hours of fermentation, the ethanol supplied culture produces a concentration of 3950 u/ml. penicillin G in the first fermentor compared to only 250 u/ml. by the non-ethanol supplied fermentation in the control fermentor.

EXAMPLE 2

Utilization Of Ethanol In The Production Of Penicillin V

Conditions of culturing are the same as described in Example 1, except potassium phenoxy acetate precursor is employed rather than potassium phenyl acetate. By 115 hours of fermentation, the ethanol-supplied culture produces a penicillin concentration of 4200 units of penicillin V per ml. compared to only 310 units/ml. by the fermentation with no ethanol feed.

These examples demonstrate that ethanol is utilized as a source of carbon and chemical energy in the fermentative production of penicillins.

What is claimed is:

1. In a fermentative process of producing penicillin by aerobically culturing a penicillin producing microorganism of the Penicillium genus in a medium containing a source of carbon and energy, a source of nitrogen, inorganic salts, and side-chain precursor followed by the step of recovering the penicillin from the medium, wherein the improvement comprises employing ethanol as the major source of carbon and chemical energy.

2. The process of claim 1 wherein the medium is at a pH of from about 5 to about 7.5 and the temperature is from about 20° C. to about 28° C. and culturing is carried out for from about 5 to about 10 days.

3. The process of claim 2 wherein the penicillin producing culture is a strain of *Penicillium chrysogenum*.

4. The process of claim 3 wherein the side-chain precursor is phenyl acetic acid or a salt thereof.

5. The process of claim 3 wherein the side-chain precursor is phenoxy acetic acid or a salt thereof.

* * * * *